US012806356B2

(12) United States Patent
Ma et al.

(10) Patent No.: US 12,806,356 B2
(45) Date of Patent: Nov. 24, 2026

(54) CUFF PRESSURE CONTROL SYSTEM AND METHOD BASED ON AIRWAY DEVICE CUFF SIZE

(71) Applicant: Covidien LP, Mansfield, MA (US)

(72) Inventors: Hongtao Ma, Shanghai (CN); Huijie Jiang, Shanghai (CN)

(73) Assignee: Covidien LP, Mansfield, MA (US)

( * ) Notice: Subject to any disclaimer, the term of this patent is extended or adjusted under 35 U.S.C. 154(b) by 482 days.

(21) Appl. No.: 18/558,334

(22) PCT Filed: May 24, 2021

(86) PCT No.: PCT/CN2021/095367

§ 371 (c)(1),
(2) Date: Oct. 31, 2023

(87) PCT Pub. No.: WO2022/246584

PCT Pub. Date: Dec. 1, 2022

(65) Prior Publication Data

US 2024/0216631 A1 Jul. 4, 2024

(51) Int. Cl.
*A61M 16/04* (2006.01)
*A61M 16/00* (2006.01)

(52) U.S. Cl.
CPC ........ *A61M 16/044* (2013.01); *A61M 16/024* (2017.08); *A61M 2016/0027* (2013.01); *A61M 2205/10* (2013.01); *A61M 2205/3327* (2013.01); *A61M 2205/3331* (2013.01); *A61M 2205/3341* (2013.01); *A61M 2205/3379* (2013.01); *A61M 2205/502* (2013.01); *A61M 2205/52* (2013.01); *A61M 2210/1032* (2013.01)

(58) Field of Classification Search
CPC ............ A61M 16/044; A61M 25/1018; A61M 25/10181; A61M 25/10184; A61M 25/10187
See application file for complete search history.

(56) References Cited

U.S. PATENT DOCUMENTS

| | | | | |
|---|---|---|---|---|
| 4,552,558 | A | 11/1985 | Muto | |
| 4,969,466 | A * | 11/1990 | Brooks | A61B 5/0225 600/490 |
| 6,171,254 | B1 * | 1/2001 | Skelton | A61B 5/022 600/490 |
| 8,226,601 | B2 * | 7/2012 | Gunday | A61M 29/02 604/96.01 |
| 10,173,022 | B1 | 1/2019 | Zachar | |

(Continued)

FOREIGN PATENT DOCUMENTS

CN 204637223 U 9/2015

OTHER PUBLICATIONS

International Search Report for International Application No. PCT/CN2021/095367 mailed Feb. 22, 2022 (5 pages).

(Continued)

*Primary Examiner* — Kathryn E Ditmer

(57) ABSTRACT

A cuff inflation controller is provided that includes a pressure sensor that generates pressure data indicative of internal pressure in a cuff and a pump that transfers inflation fluid to or from the cuff. A controller of the cuff inflation controller operates to determine a size of the cuff based on data from the pressure sensor and to set control parameters for the pump based on the determined cuff size.

20 Claims, 5 Drawing Sheets

(56) References Cited

U.S. PATENT DOCUMENTS

| | | | | |
|---|---|---|---|---|
| 2010/0163023 | A1* | 7/2010 | Singh .................. | A61M 16/044 73/1.01 |
| 2010/0252048 | A1* | 10/2010 | Young ................. | A61M 16/024 128/207.15 |
| 2012/0197086 | A1 | 8/2012 | Morris et al. | |
| 2015/0314092 | A1* | 11/2015 | Kimm ................. | A61M 16/044 128/207.15 |
| 2016/0022939 | A1 | 1/2016 | Wood et al. | |
| 2018/0177937 | A1* | 6/2018 | Eliasson ............. | A61M 3/0295 |

OTHER PUBLICATIONS

International Written Opinion for International Application No. PCT/CN2021/095367 mailed Feb. 22, 2022 (4 pages).

* cited by examiner

CUFF PRESSURE CONTROL SYSTEM AND METHOD BASED ON AIRWAY DEVICE CUFF SIZE

This application is a National Stage Application of PCT/CN2021/095367 filed May 24, 2021, which application is incorporated herein by reference. To the extent appropriate, a claim of priority is made to the above disclosed application.

BACKGROUND

The present disclosure relates generally to medical devices and, more particularly, to systems and related methods for controlling pressure in cuffs associated with tracheal tubes or other airway devices.

This section is intended to introduce the reader to various aspects of art that may be related to the present disclosure, as described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, airways devices such as tracheal tubes may be used to control the flow of respiratory gases through a patient's trachea. Such tracheal tubes may include endotracheal (ET) tubes, tracheostomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of gases flowing into and out of the patient. An inflatable cuff may be associated with these tubes, and the seal can be established by inflating the cuff around the tube and maintaining the internal pressure in the cuff while the airway device is in use.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In one embodiment, a cuff inflation controller includes a pressure sensor that generates pressure data indicative of internal pressure in a cuff and a pump that transfers inflation fluid to or from the cuff. The cuff inflation controller includes a controller that operates to receive first pressure data from the pressure sensor; control the pump to transfer a volume of inflation fluid to the cuff to change the internal pressure in the cuff; receive second pressure data from the pressure sensor in response to changing the internal pressure in the cuff; determine a size of the cuff based on the first pressure data and the second pressure data; and set control parameters for the pump based on the determined size of the cuff.

In an embodiment, a method is provided that includes the steps of receiving first pressure data from a pressure sensor fluidically coupled to a cuff of an airway device; controlling a pump to transfer a volume of inflation fluid to the cuff to change an internal pressure in the cuff; receiving second pressure data from the pressure sensor in response to changing the internal pressure in the cuff; determining a size of the cuff based on the first pressure data and the second pressure data; and setting control parameters for the pump based on the determined size of the cuff.

In an embodiment, a cuff inflation controller includes a pressure sensor and a pump. The cuff inflation controller also includes a controller that operates to determine a size of a first cuff based on cuff calibration pressure data of the first cuff from the pressure sensor; set first control parameters for the pump based on the determined size of the first cuff; determine a size of a second cuff based on cuff calibration pressure data of the second cuff from the pressure sensor; and set second control parameters for the pump based on the determined size of the second cuff.

Features in one aspect or embodiment may be applied as features in any other aspect or embodiment, in any appropriate combination. For example, any one of system, laryngoscope, controller (e.g., processor-based controller), external sensor, or method features may be applied as any one or more other of system, laryngoscope, controller, external sensor, or method features.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
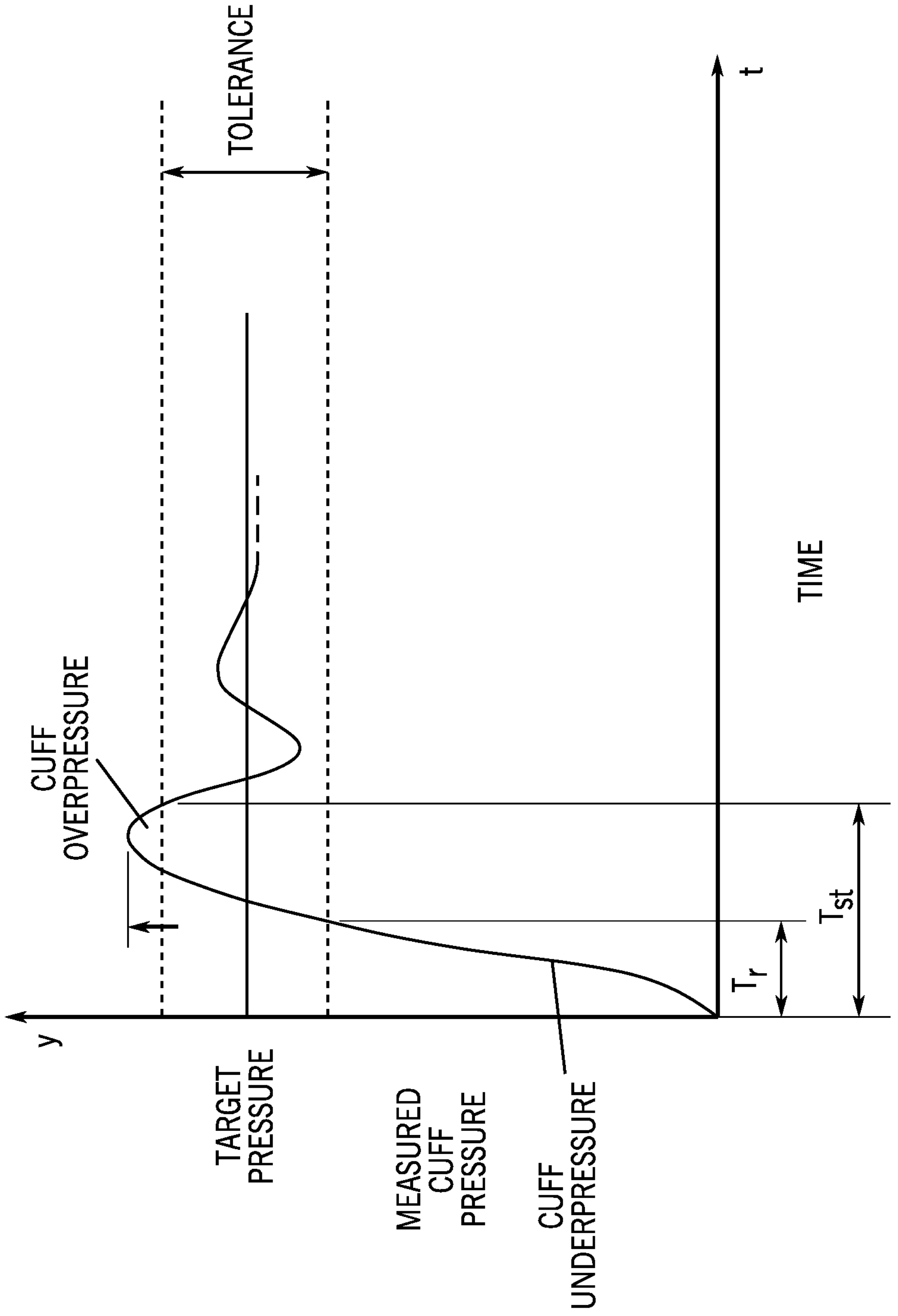
FIG. 1 shows an example of cuff pressure over time in response to pressure changes caused by using a pump of a cuff inflation controller, in accordance with certain embodiments of the disclosure.

A tracheal tube is used to transfer respiratory gases from a ventilator to a patient when inserted into a patient's trachea. After positioning the tracheal tube at a desired position within the trachea, a cuff is inflated around the tracheal tube to seal the tracheal passage at a pressure that sufficiently seals the airway but that avoids patient discomfort. Over the course of ventilating the patient, stable sealing pressure in the cuff should be maintained to facilitate efficient gas delivery and to avoid leakage of upper airway secretions from above the cuff into the lungs. Accordingly, a caregiver can periodically check the cuff pressure and perform a manual adjustment, e.g., via a syringe, when the cuff pressure has deviated from a desired target pressure. In another example, an automatic cuff inflation controller can be coupled to the cuff to monitor the cuff pressure and to automatically adjust the cuff pressure in response to deviation from a target pressure by adding or removing inflation fluid until the target pressure is reestablished.

Automatic monitoring and adjustment of cuff pressure using a cuff inflation controller can provide more stable cuff pressures for a ventilated patient because deviations from a target pressure are quickly identified and resolved. A detected cuff pressure deviation from the target pressure causes the cuff inflation controller to activate according to control parameters that control pump output to adjust the pressure based on the magnitude of the detected deviation. A larger detected deviation may cause the pump to operate with proportionally greater output relative to a smaller deviation from target pressure. However, the cuff inflation controller may overshoot or undershoot the target pressure during the adjustment process, leading to temporary cuff overpressure and/or underpressure until a correction is applied. Further overpressure and underpressure may be more pronounced for cuffs that are smaller or larger than an average cuff size used in tuning the control parameters.

Provided herein are cuff pressure control techniques that use cuff size as an input to set control parameters of a cuff inflation controller. Different tracheal tube sizes are available to accommodate patients having different airway anatomies, e.g., based on patient size and/or age. For example, endotracheal tubes may be sized according to their tube inner diameters, with sizes ranging from 3.0 mm to 10.0 mm in embodiments. Different tube sizes are associated with different cuff sizes, with larger diameter tubes having attached larger cuffs (i.e., having a larger internal volume when fully inflated) relative to smaller diameter tubes that have attached smaller cuffs (i.e., having a smaller internal volume when fully inflated). Accordingly, the pump output needed to fully inflate or adjust an internal cuff pressure without overshooting the target pressure may vary depending on the size of the cuff. The disclosed techniques provide more reliable cuff pressure maintenance that uses cuff size as an input to set control parameters of a pump of the cuff pressure controller to avoid temporary overpressure and/or underpressure of the cuff while adjusting internal cuff pressure.

The disclosed techniques, in an embodiment, include a cuff inflation controller that determines a size of a coupled cuff by detecting cuff pressure changes in response to transfer of a fixed or known volume of inflation fluid. The detected cuff pressure change is a characteristic of the cuff volume, which can be used to determine the cuff size as part of a calibration process. The cuff size, in turn, is used to set the control parameters of a pump that are tuned to that particular cuff size. The use of variable control parameters based on detected cuff size in a cuff inflation controller improves overall cuff pressure stability.

FIG. 1 shows an example of cuff pressure over time in response to pressure changes caused by using a pump of a cuff inflation controller to change or adjust cuff pressure and operating under a feedback control loop. In response to the detected deviation from the set cuff target pressure, the cuff inflation controller responds by controlling the pump to adjust the pressure in the cuff.

Pump control parameters that result in an increased pump output may cause a faster adjustment by causing a faster inflation fluid transfer into the cuff. However, the faster transfer rate may result in a pressure overshoot. The volume of inflation fluid used to correctly adjust the cuff pressure varies depending on the size of the cuff. Accordingly, the pump output used to adjust pressure for a larger cuff size may cause overpressure in a smaller cuff size, as shown by way of example in FIG. 1. While the overpressure in the smaller cuff can be subsequently corrected by the cuff inflation controller, repeated temporary periods of cuff overpressure may cause discomfort for the patient. Further, if the correction from overpressure is tuned or calibrated to a larger cuff, the cuff inflation controller may remove too much inflation fluid in response to overpressure, causing a temporary cuff underpressure. This in turn may lead to pressure oscillations in the cuff, which extends the settling time to a stable cuff pressure. Similarly, if the pump output of the cuff inflation controller is tuned to a relatively smaller cuff, adjustment in response to a detected low pressure may have a slower rise time, which extends the underpressure time of the cuff.

Provided herein are cuff pressure control systems and methods that use variable pump control parameters based on cuff size to maintain pressure stability in the cuff. The variable pump control parameters are tuned to for each individual cuff size to achieve desired rise times (Tr) from a starting pressure to the target pressure, minimize overshoot of a cuff target pressure, and have faster settling times (Tst) to a state at which oscillations between pressures above and below the target pressure are below a threshold and a stable cuff pressure is achieved.

Figure 2:
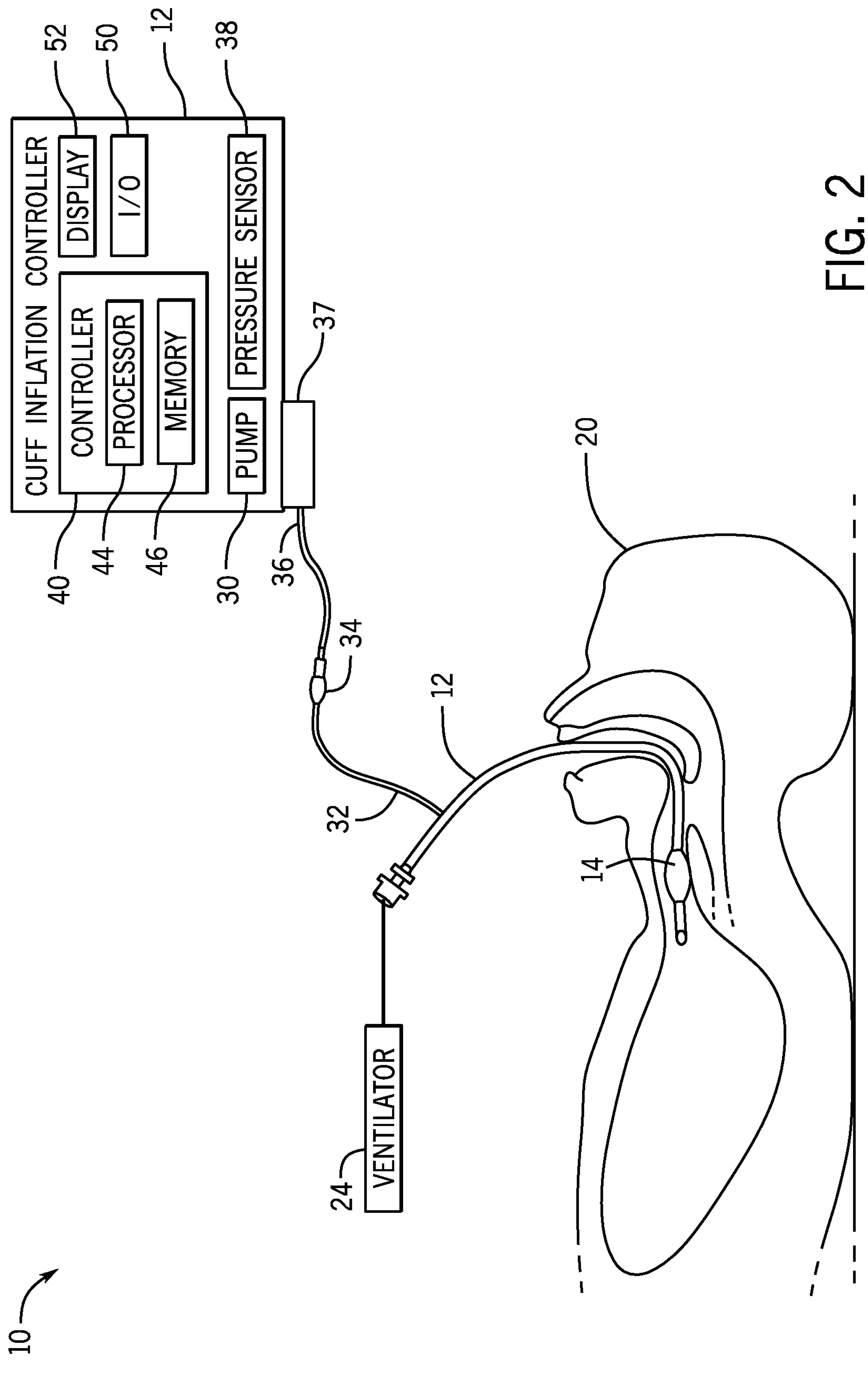
FIG. 2 is a schematic illustration of a cuff pressure system, in accordance with certain embodiments of the disclosure.

FIG. 2 shows an automatic cuff pressure control system 10 according to the disclosed embodiments that includes a cuff inflation controller 12 coupled to a cuff 14 of a tracheal tube 16. In the depicted example, the tracheal tube 16 is inserted in an airway of a patient 20, and the cuff 14 is inflated to seal the airway. The tracheal tube 16 can be coupled to a ventilator 24 that transfers respiratory gases through the tracheal tube 16 to ventilate the patient. While the depicted cuff inflation controller 12 is shown as a separate or standalone device, it should be understood that the cuff inflation controller 12 may be part of or housed within the ventilator 24 in embodiments.

The cuff inflation controller 12 is fluidically coupled to the cuff 14, and a pump 30 transfers inflation fluid to or from the cuff 14 to change an internal cuff pressure, e.g., to inflate the cuff 14, to deflate the cuff 14, or to adjust the cuff pressure to a target pressure. The cuff 14 includes an inflation line 32 terminating in a connector 34 that couples to the cuff inflation controller 12 to facilitate fluidic communication. In the depicted embodiment, the coupling is via an extension tube 36 connected to a port 37 of the cuff inflation controller 12. In operation, the user positions the tracheal tube 16 in the airway to intubate the patient 20. Once the tracheal tube 16 is correctly positioned, the user can couple the connector 34 of the inflation line 32 to the cuff inflation controller 12, and the cuff inflation controller 12 activates the pump 30 to inflate the cuff 14 to a target cuff pressure (e.g., an internal cuff pressure set between 20 to 30 cm $H_2O$) to seal the airway. The user can also connect the tracheal tube 16 to a breathing circuit of the ventilator 24 to initiate ventilation.

Over the course of ventilation, the internal pressure of the cuff 14 can deviate from the target cuff pressure. For example, the cuff pressure may change as a result of patient movement or repositioning, swelling in the trachea, infiltration of nitrous oxide in respiratory gases into the cuff 14, or exterior pressure differences over the course of a breathing cycle. The cuff inflation controller 12 monitors the cuff pressure using a pressure sensor 38 fluidically coupled to the cuff 14. The pressure sensor generates data indicative of an internal cuff pressure. Deviations from a set target pressure cause the cuff inflation controller 12 to automatically adjust the cuff pressure by activating the pump 30 to add inflation fluid to increase the cuff pressure or to remove inflation fluid to decrease the cuff pressure. The inflation controller 12 measures pressure of the cuff 14 using the pressure sensor 38 and, in an embodiment, automatically adjusts the pressure to maintain an internal cuff pressure at the cuff target pressure. In an embodiment, the cuff inflation controller 12 maintains the cuff pressure in a preset range or within a tolerance (e.g., within 1-3%) of the cuff target pressure.

The cuff inflation controller 12 includes a controller 40. The controller 40 executes hardware and/or software control algorithms to identify deviations from the target cuff pressure, activate or deactivate the pump 30, determine a size of the cuff 14, set control parameters of the pump 30, opening or closing valves of a pump system, and/or provide control instructions to the pump 30 to operate according to variable control parameters as provided herein. The controller 40 may include processor(s) 44 (e.g., general purpose microprocessors, special-purpose microprocessors, processing circuitry implemented as a FPGA and/or ASIC) that execute software programs to control operations as disclosed herein. The controller 40 may include a memory device 46 such as a random access memory or a read-only memory storing executable instructions. In an embodiment, the memory device 46 stores a lookup table of one or more control parameters of the pump 30 associated with different cuff sizes.

The cuff inflation controller 12 includes a user interface 50 (e.g., a control screen of a display 52 and/or dedicated buttons or keys) that receives user inputs such as cuff target pressure inputs of a user. The target pressure can be set by a user via the user interface 50 and/or can be a default target pressure stored in the memory 46. The target pressure can be stored in the memory 46 of the controller 40. The cuff inflation controller 12 may, in an embodiment, include communication circuitry (e.g., wireless or wired communication circuitry) to communicate measured cuff pressure, determined cuff size, or other information to coupled devices of the system 10.

Figure 3:
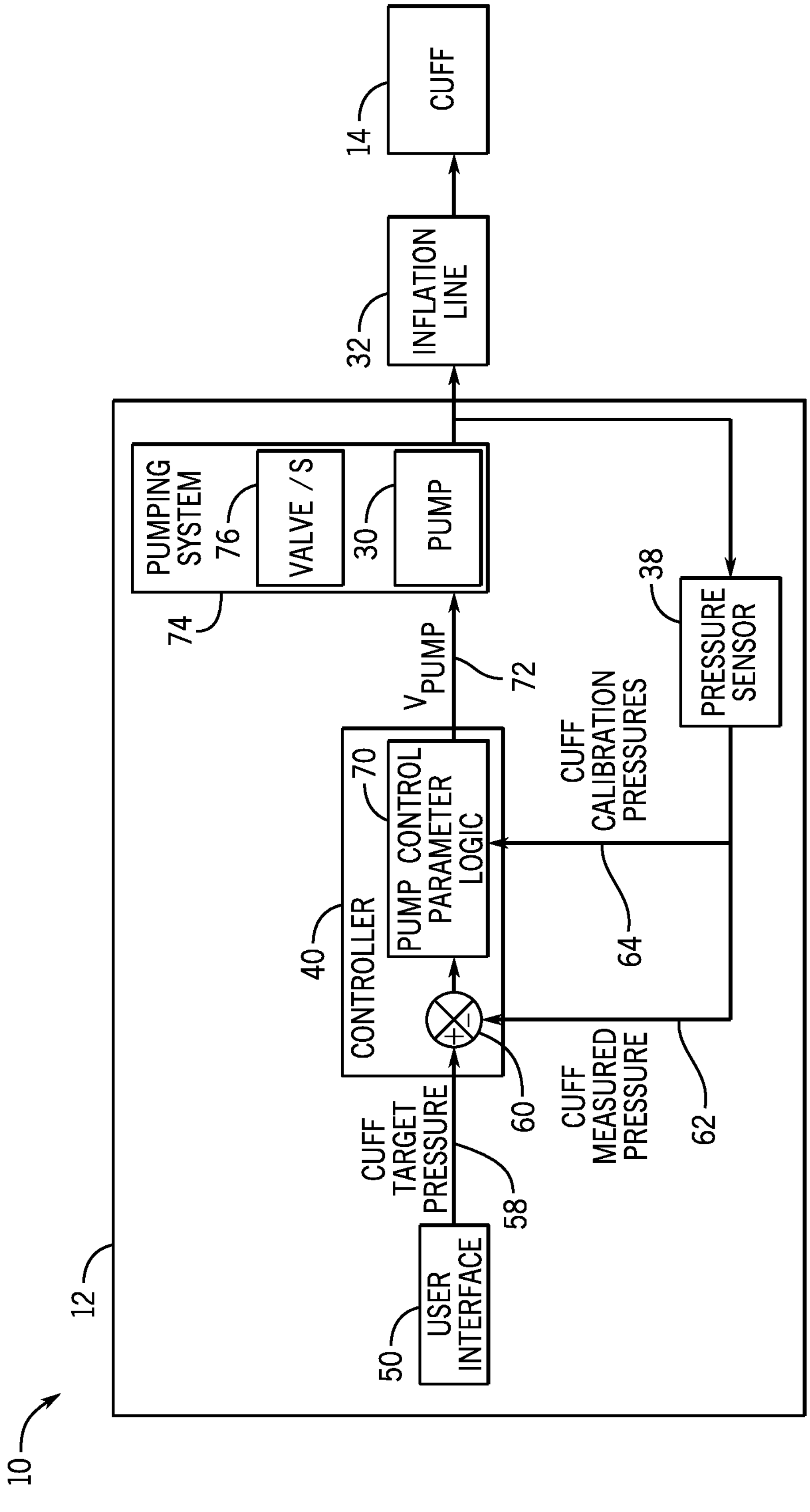
FIG. 3 is a block diagram of components of the cuff pressure system of FIG. 2, in accordance with certain embodiments of the disclosure.

FIG. 3 is a block diagram of certain components of the cuff pressure control system 10. The cuff inflation control 12 includes a user interface 50 that permits an input of a cuff target pressure 58. Additionally or alternatively, the cuff inflation controller 12 may store or provide a default cuff target pressure 58. The cuff target pressure 58 is provided to the controller 40, and a difference calculator 60 determines if there is a difference between the cuff target pressure 58 and the measured cuff pressure 62.

In addition, the controller 40 can control a cuff size determination process, e.g., a cuff calibration, that determines the size of the coupled cuff 14, and as generally discussed with reference to FIG. 4. As part of the cuff size determination process, the controller drives the pump 30 to transfer a fixed or known volume of inflation fluid to the cuff 14 via inflation line 32. The pressure sensor 38 measures the cuff pressure before and after the volume of inflation fluid is transferred to the cuff 14 to generate cuff calibration pressures 64. The cuff calibration pressures 64 are provided to pump control parameter logic 70 to determine a size of the cuff, and the size of the cuff 14 is used to set control parameters to generate drive or control instructions 72 for the pump 30. The control instructions 72 may also be based on the magnitude of an identified deviation between the cuff target pressure 60 and the measured cuff pressure 62.

In an embodiment, the pump 30 is part of a pumping system 74 that includes the pump 30 and one or more valves 76. For example, the pump 30 may be single direction pump, and the pumping system 74 may include a first valve 76 and a second valve 76 that are respectively used to change the flow direction of the pump 30 to or from the cuff 14 to realize inflation or deflation. The controller 40 may also control selective activation of the appropriate valve 76 (e.g., to or from the cuff 14) to control the direction of fluid flow to cause inflation or deflation. The pump 30 operates under at least one of proportional-integral-derivative (PID) control. Factors in the control parameters of the pump in a PID control may include a proportional (P) control mode that generates a larger pump output when the measured deviation is larger and a smaller pump output when the measured deviation is smaller. The PID control may also include an integral (I) control mode representative of the area under the curve of cuff pressure deviation from the target pressure (e.g., to assess short duration but large magnitude pressure variation and smaller magnitude sustained periods of pressure deviation) and a derivative (D) control mode based on a rate of change of the pressure in the cuff (e.g., a rapidly changing cuff pressure vs. a slowly changing cuff pressure). Each control mode in the PID control algorithm is associated with a respective control parameter value, such as a gain setting.

In operation, each control parameter in the PID control is multiplied by the error or difference between the measured pressure 62 and the cuff target pressure 58 to generate control instructions 72 for the pump 30. The pump 30 can operate under closed loop control such that the pressure change caused by the adjustment is measured and fed into new instructions for controlling the pump 30. Thus, in the case of PID control, the value of the pressure difference changes as a result of adjustment, and the new value representative of the updated deviation from the target pressure is multiplied by the P, I, and/or D control parameters to generate the updated control instructions 72 for the pump 30. It should be understood that the pump 30 may operate under any combination of PID control, using any one, any two, or all three of P, I, or D control parameters to generate the control instructions 72.

As provided herein, the one or more of the individual control parameters for P, I, and/or D can vary between different cuff sizes. Accordingly, the pump control parameter logic 70, in an embodiment, uses the cuff calibration pressures 64 to determine a cuff size and calculates or selects P, I, and/or D control parameters associated with the determined cuff size. The individual control parameters for P, I, and/or D for each cuff size can be determined empirically. In an embodiment, the control parameters are tuned to avoid overshooting the cuff pressure and to desired rise times or settling times (see FIG. 1) for cuffs of different sizes. In contrast to systems that use a fixed set of parameters that are tuned to an average cuff size for cuffs of varying sizes, the disclosed cuff pressure control techniques vary the control parameters used by the pump 30 based on the determined cuff size. Thus, the cuff inflation controller 12 operates the pump 30 to adjust the cuff pressure for each cuff 14 using parameters that are calibrated for that particular cuff size.

The pump 30 may additionally or alternatively operate under an on-off control, in which the pump 30 is controlled to adjust the pressure while the pressure deviation is detected. The pump may be set to a lower output for smaller cuff sizes relative to larger cuff sizes during the on-cycle.

Figure 4:
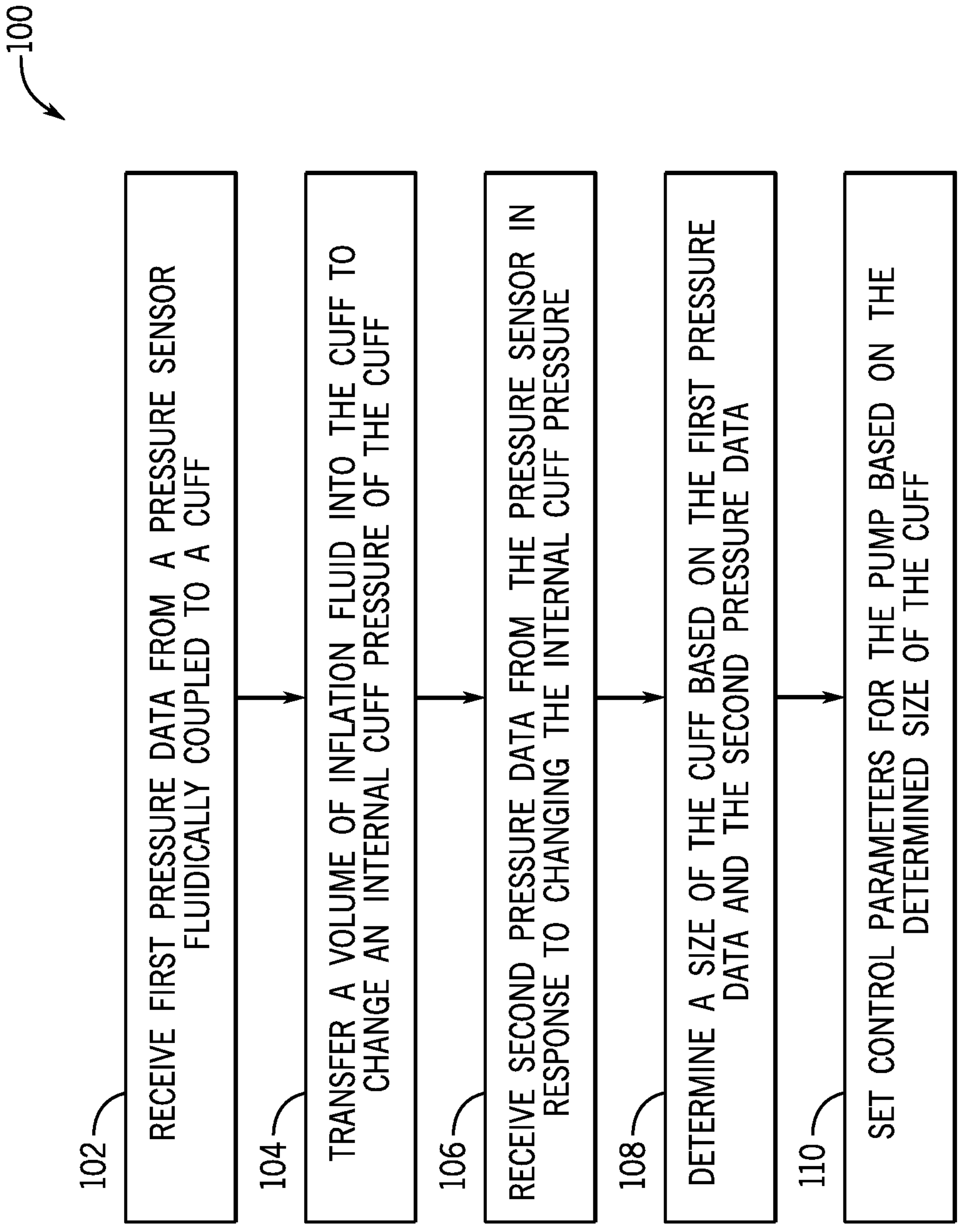
FIG. 4 is a flow diagram of a method of setting control parameters of a pump of a cuff inflation controller, in accordance with certain embodiments of the disclosure.

FIG. 4 is a flow diagram of a method of setting control parameters of the pump 30 of the cuff inflation controller 12 based on a determination of cuff size. The method is generally indicated by reference number 100 includes various steps or actions represented by blocks. Certain elements of FIG. 4 are discussed with reference to elements illustrated in FIGS. 2-3. It should be noted that the method 100 may be performed as an automated procedure by the cuff inflation controller 12. In an embodiment, the method 100 may be performed as a calibration step prior to intubating the patient and while the tracheal tube 16 is outside of the patient. However, in an embodiment, the method 100 may be performed while the tracheal tube 16 is positioned in the patient airway.

The method 100 receives first pressure data from the pressure sensor 38 (block 102) that is indicative of the internal cuff pressure of a cuff 14 that is fluidically coupled to the cuff inflation controller 12. In an embodiment, the cuff inflation controller 12 controls the cuff pressure to a fixed or preset initial pressure to start the method 100, and the first pressure data is indicative of the fixed or preset initial pressure. The fixed or preset initial pressure may be relatively low, e.g., less than 10 cm $H_2O$. The cuff inflation controller 12 controls the pump 30 to transfer a fixed or preset volume of inflation fluid into the cuff 14 to change the internal pressure of the cuff 14 (block 104), and the pressure sensor 38 measures second pressure data indicative of the change in internal pressure (block 106). The fixed volume can be selected so that the internal pressure represented in the second pressure data has a resolvable dynamic range for different cuff sizes. Accordingly, the second pressure may be relatively low, e.g., in a range of 5-15 cm $H_2O$, depending on the cuff size.

Based on the difference between the first pressure data and the second pressure data, a size of the cuff is determined (block 108) The pressure change in the cuff 14 caused by the transfer of the volume of inflation fluid is a function of the size of the cuff 14. In an embodiment, the cuff size is determined by matching the measured pressure change of the cuff to an empirically determined characteristic pressure change at the same initial pressure and after transfer of the same volume of inflation fluid that is associated with a known cuff size. In another embodiment, a cuff volume is calculated based on the pressure change and the volume of transferred inflation fluid, and the cuff volume is matched to known volumes of different cuff sizes. In an embodiment, the cuff size is a cuff size associated with a tracheal tube having a particular size. Thus, the cuff size may be a 3 mm tracheal tube cuff size, a 4 mm tracheal tube cuff size, etc.

Control parameters of the pump 30 are set based on the determined cuff size (block 110). For example, the determined cuff size is used to select control parameters stored in a lookup table and associated with the determined cuff size. If the determined cuff size does not match stored cuff sizes, control parameters associated with a closest matching cuff are used. The selected control parameters and/or the determined cuff size can be stored in a memory 46 of the controller 40 and used to generate control instructions 72 for the pump 30 while the cuff 14 is coupled to the inflation controller 12. The cuff inflation controller 12 monitors pressure in the cuff 14 while the patient is intubated and controls the pump 30 using the set control parameters.

While the cuff calibration can be performed prior to intubation, the steps of the calibration may additionally or alternatively be performed after intubation. For example, the calibration may be performed during initial cuff inflation. The cuff inflation controller 12 can measure inflation pressure at a first pressure of the cuff 14, transfer a known volume of inflation fluid to the cuff 14 and measure the second pressure, and then complete the inflation to the set target pressure to seal the airway.

Figure 5:
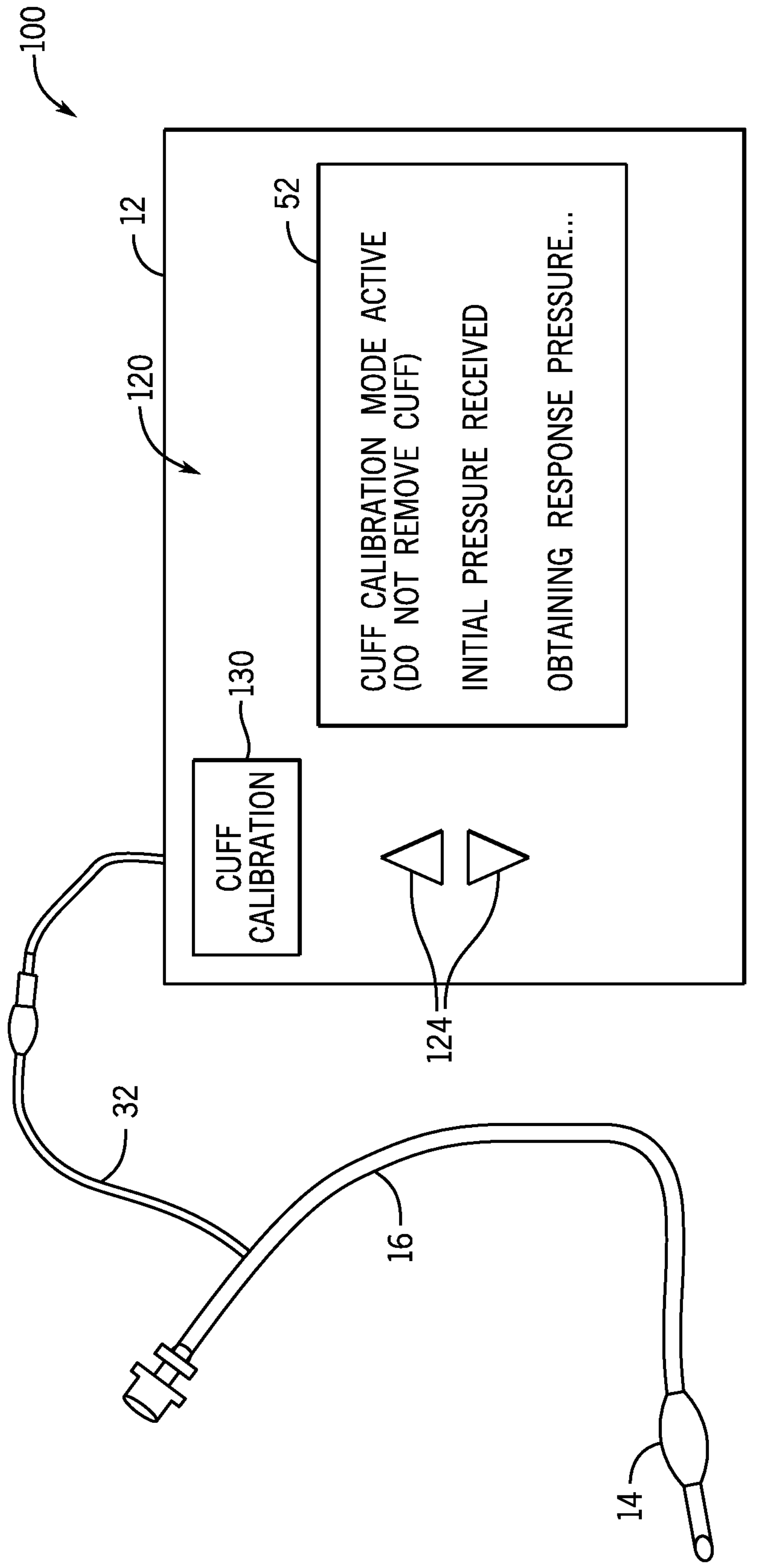
FIG. 5 is an example user interface of a cuff inflation controller performing a cuff calibration to determine a cuff size and set control parameters of a pump, in accordance with certain embodiments of the disclosure.

FIG. 5 is an example user interface 120 of a cuff inflation controller 12 that includes the display screen 52 and target pressure adjustment buttons 124. The user interface includes a cuff calibration mode input, shown as a button 130. The cuff calibration mode input may alternatively be a selectable option on the display screen 52. The cuff calibration mode causes the cuff inflation controller 12 to perform cuff calibration steps (see FIG. 4) to recognize the size of the cuff 14 and set control parameters of the pump 30.

The display screen 52 can display notifications and guidance for the user to indicate that one or more calibration steps are in progress. For example, the user can be guided to couple the inflation line 32 to the inflation controller 12 and to position the tracheal tube to permit pressure adjustment during calibration without squeezing the cuff 14.

In an embodiment, the user may be permitted to manually enter the cuff size (e.g., by entering the tracheal tube size) via the user interface 120, and the cuff inflation controller 12 can set the control parameters based on the manual entry.

Initiation of a new calibration via the calibration mode input 130 may automatically erase any previously stored cuff size and/or previously set control parameters. In another embodiment, powering up after shutdown of the cuff inflation controller will result in the previously stored cuff size and/or previously set control parameters being erased. In the event that the user does not perform the cuff calibration, the cuff inflation controller 12 can apply default control parameters and/or generate a notification to perform the calibration. In certain embodiments, the cuff inflation controller 12 automatically performs the calibration without user input.

In certain embodiments, the disclosed cuff pressure control systems and methods may be used in conjunction with any appropriate medical device, including, without limitation, a feeding tube, an endotracheal tube, an endobronchial tube, a tracheostomy tube, a nasal cannula, and/or a supraglottic mask/tube. The present techniques may also be used to monitor any patient benefiting from mechanical ventilation, e.g., positive pressure ventilation.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

What is claimed is:

1. A cuff inflation controller for an airway device comprising:

a pressure sensor that is configured to generate pressure data indicative of internal pressure in a cuff of the airway device;

a pump that is configured to transfer inflation fluid to or from the cuff;

a controller that is configured to operate to:

receive first pressure data from the pressure sensor;

control the pump to transfer a volume of inflation fluid to the cuff to change the internal pressure in the cuff;

receive second pressure data from the pressure sensor in response to changing the internal pressure in the cuff;

determine a fully inflated size of the cuff based on the first pressure data and the second pressure data; and set control parameters for the pump based on the determined fully inflated size of the cuff.

2. The cuff inflation controller of claim 1, wherein the controller is configured to operate to:

receive third pressure data from the pressure sensor, wherein the third pressure data is indicative of a deviation of the internal pressure from a target cuff pressure; and control the pump using the set control parameters to adjust the internal cuff pressure to the target cuff pressure.

3. The cuff inflation controller of claim 2, comprising a user interface that is configured to receive a user input of the target cuff pressure.

4. The cuff inflation controller of claim 1, wherein the controller is configured to operate to store the determined fully inflated cuff size in a memory.

5. The cuff inflation controller of claim 4, wherein the controller is configured to operate to erase a previously stored fully inflated cuff size from the memory in response to determining the fully inflated cuff size.

6. The cuff inflation controller of claim 4, wherein the controller is configured to operate to erase a previously stored fully inflated cuff size from the memory in response to receiving an input indicative of a calibration mode.

7. The cuff inflation controller of claim 1, wherein the control parameters for the pump comprise one or more gain settings of a proportional-integral-derivative control algorithm.

8. The cuff inflation controller of claim 1, wherein the control parameters for the pump comprise control parameters of an on-off control algorithm.

9. The cuff inflation controller of claim 1, wherein the volume of inflation fluid comprises a fixed or preset volume.

10. The cuff inflation controller of claim 1, comprising a connector or port that fluidically couples to an inflation line of the cuff, wherein the inflation fluid is configured to be transferred by the pump to or from the cuff via the inflation line.

11. The cuff inflation controller of claim 1, wherein a first set of control parameters is associated with a first determined fully inflated cuff size and a second set of control parameters is associated with a second determined fully inflated cuff size, wherein the first determined fully inflated cuff size is larger than the second determined fully inflated cuff size.

12. The cuff inflation controller of claim 1, wherein the first pressure data is indicative of a first internal pressure of the cuff, wherein the second pressure data is indicative of a second internal pressure of the cuff, and wherein the first internal pressure and the second internal pressure are below 15 cm $H_2O$.

13. A method of controlling cuff pressure in an airway device, comprising:

receiving first pressure data from a pressure sensor fluidically coupled to a cuff of the airway device;

controlling a pump to transfer a volume of inflation fluid to the cuff to change an internal pressure in the cuff;

receiving second pressure data from the pressure sensor in response to changing the internal pressure in the cuff;

determining a fully inflated size of the cuff based on the first pressure data and the second pressure data; and setting control parameters for the pump based on the determined fully inflated size of the cuff.

14. The method of claim 13, wherein determining the fully inflated size of the cuff comprises calculating a cuff volume based on the first pressure data, the second pressure data, and the volume of inflation fluid, and fitting the calculated cuff volume to a fully inflated cuff size.

15. The method of claim 13, wherein setting the control parameters for the pump comprises using a lookup table to select control parameters corresponding to the determined fully inflated size of the cuff.

16. The method of claim 13, comprising adjusting the internal pressure in the cuff to a preset initial pressure and receiving the first pressure data in response to the adjusting.

17. The method of claim 13, comprising:

receiving third pressure data from the pressure sensor, wherein the third pressure data is indicative of a deviation of the internal pressure from a target cuff pressure; and controlling the pump using the set control parameters to adjust the internal pressure to the target cuff pressure.

18. A cuff inflation controller for an airway device, comprising:

a pressure sensor that is configured to generate pressure data indicative of internal pressure in a cuff of the airway device;

a pump configured to transfer inflation fluid to or from the cuff;

a controller that is configured to operate to:

determine a fully inflated size of a first airway device cuff based on cuff calibration pressure data of the first airway device cuff from the pressure sensor;

set first control parameters for the pump based on the determined fully inflated size of the first airway device cuff;

determine a fully inflated size of a second airway device cuff based on cuff calibration pressure data of the second airway device cuff from the pressure sensor; and set second control parameters for the pump based on the determined fully inflated size of the second airway device cuff.

19. The cuff inflation controller of claim 18, wherein the first control parameters comprise a first proportional gain setting and the second control parameters comprise a second proportional gain setting different than the first proportional gain setting.

20. The cuff inflation controller of claim 18, wherein an output of the pump is configured to be different when operating under the first control parameters relative to the second control parameters.

* * * * *